United States Patent
Schena et al.

(10) Patent No.: US 8,151,661 B2
(45) Date of Patent: Apr. 10, 2012

(54) COMPACT CAPSTAN

(75) Inventors: Bruce Schena, Menlo Park, CA (US); Thomas G Cooper, Menlo Park, CA (US)

(73) Assignee: Intuituve Surgical Operations, Inc., Sunnyvale, CA (US)

( * ) Notice: Subject to any disclaimer, the term of this patent is extended or adjusted under 35 U.S.C. 154(b) by 1283 days.

(21) Appl. No.: 11/428,251

(22) Filed: Jun. 30, 2006

(65) Prior Publication Data

US 2008/0009838 A1    Jan. 10, 2008

(51) Int. Cl.
*F16H 19/06* (2006.01)
(52) U.S. Cl. .................. 74/89.22; 242/157.1; 242/397.3
(58) Field of Classification Search .................. 74/89.2, 74/89.22; 187/267; 242/157.1, 397.2, 397.3; 254/331
See application file for complete search history.

(56) References Cited

U.S. PATENT DOCUMENTS

| | | | | |
|---|---|---|---|---|
| 150,612 A * | 5/1874 | Reedy | ............................ | 187/261 |
| 238,762 A * | 3/1881 | Clayton | ........................ | 187/263 |
| 652,893 A * | 7/1900 | Herdman | .................... | 254/276 |
| 1,110,248 A * | 9/1914 | Atwood | ........................ | 226/193 |
| 1,811,623 A * | 6/1931 | Ferguson | ..................... | 254/331 |
| 1,866,911 A * | 7/1932 | Schroeder | ..................... | 226/193 |
| 2,598,709 A * | 6/1952 | Morris | ......................... | 74/89.14 |
| 2,802,638 A * | 8/1957 | Ireland | ......................... | 242/470 |
| 2,868,504 A * | 1/1959 | Minty | ........................... | 242/398 |
| 2,942,879 A | 6/1960 | Izenour | | |
| 3,339,753 A * | 9/1967 | Forster et al. | ................. | 212/312 |
| 3,545,725 A * | 12/1970 | Chandler et al. | .............. | 254/331 |
| 3,673,817 A * | 7/1972 | Doran et al. | .................. | 464/168 |
| 3,804,370 A * | 4/1974 | Woodard | ...................... | 254/331 |
| 4,087,060 A * | 5/1978 | Laky et al. | ................. | 242/399.1 |
| 4,324,386 A * | 4/1982 | Gagnon et al. | ................ | 254/288 |
| 4,351,197 A * | 9/1982 | Carson | ......................... | 74/89.22 |
| 4,695,010 A | 9/1987 | Smith | | |
| 4,972,778 A * | 11/1990 | Suominen | ..................... | 104/183 |
| 6,997,442 B2 | 2/2006 | Hoffend, Jr. | | |

FOREIGN PATENT DOCUMENTS

GB    2296481 A    7/1996

OTHER PUBLICATIONS

Vertut, Jean and Philippe Coiffet, *Teleoperation and Robotics: Evolution and Development*, English translation Prentice-Hall, Inc., Inglewood Cliffs, NJ, USA, 1986.

* cited by examiner

*Primary Examiner* — William C Joyce (57) ABSTRACT

A compact capstan includes a drum, a coupled hub, a passage extending through the drum and hub, and a shaft extending through the drum and hub. The shaft engages the passage such that the shaft can transmit a torsional force to the drum and the hub which are free to move along the length of the shaft. The drum includes a spiral groove to receive a cable loop wound around the drum. The hub has a thread with substantially the same pitch as the spiral groove to engage a threaded support such that the hub and the drum move laterally along their length relative to the threaded support as the hub and the drum are rotated. The shaft has a length that is substantially greater than the passage such that the shaft extends beyond both ends of the passage.

19 Claims, 8 Drawing Sheets

COMPACT CAPSTAN

FIELD

The embodiments of the invention are generally related to robotic surgical systems. More particularly, the embodiments of the invention relate to cable drive systems for robotic surgical arms.

BACKGROUND OF THE INVENTION

Minimally invasive surgery (MIS) provides surgical techniques for operating on a patient through small incisions using a camera and elongate surgical instruments introduced to an internal surgical site, often through trocar sleeves or cannulas. The surgical site often comprises a body cavity, such as the patient's abdomen. The body cavity may optionally be distended using a clear fluid such as an insufflation gas. In traditional minimally invasive surgery, the surgeon manipulates the tissues using end effectors of the elongate surgical instruments by actuating the instrument's handles while viewing the surgical site on a video monitor.

A common form of minimally invasive surgery is endoscopy. Laparoscopy is a type of endoscopy for performing minimally invasive inspection and surgery inside the abdominal cavity. In standard laparoscopic surgery, a patient's abdomen is insufflated with gas, and cannula sleeves are passed through small (generally ½ inch or less) incisions to provide entry ports for laparoscopic surgical instruments. The laparoscopic surgical instruments generally include a laparoscope (for viewing the surgical field) and working tools.

The working tools are similar to those used in conventional (open) surgery, except that the working end or end effector of each tool is separated from its handle by a tool shaft. As used herein, the term "end effector" means the actual working part of the surgical instrument and can include clamps, graspers, scissors, staplers, image capture lenses, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in other types of surgeries such as arthroscopy, retroperitoneoscopy, pelviscopy, nephroscopy, cystoscopy, cisternoscopy, sinoscopy, hysteroscopy, urethroscopy, and the like.

Endoscopy may be performed with robotically controlled working tools. Robotic control may provide an improved control interface to the surgeon. Robotically controlled working tools may be driven by servo mechanisms, such as servo motors, that are coupled to the working tool by mechanical cables. Each servo mechanism may be coupled to a cable by a capstan that draws in and pays out the cable wound around the capstan. The cable may be routed to and from the capstan by one or more pulleys. The cable may rotate a driver that is coupled to the robotically controlled working tool to drive and control movement of the tool. As space in the surgical field where robotically controlled working tools are being used is at a premium, it is desirable to have a compact mechanism to drive and control the robotically controlled working tools.

In a typical cable drive system for a robotically controlled working tool, a cable is guided by a pulley and wound onto a capstan that is rigidly fixed to a shaft. The capstan being rigidly fixed to the shaft it can only be rotated with the shaft. As a result, the point at which the cable comes onto the capstan moves along the length of the capstan as the capstan rotates. If the capstan is close to the pulley guiding the cable, a large angle can be created in the cable at a take off point at the capstan. If this angle is too large, the cable may wear excessively, incur physical damage to its cable strands, run off the take off pulley, or run out of a groove in the capstan. By increasing a distance between the capstan and the pulley, the angle at the take off point may be reduced and be acceptable. However, this makes the cable drive system less compact. It is desirable to minimize the angle in the cable at the take off point of the capstan while at the same time providing a compact mechanism to drive and control movement of a robotically controlled working tool.

It will be appreciated that all the drawings of Figures provide for herein are for illustrative purposes only and do not necessarily reflect the actual shape, size, or dimensions of the elements being illustrated.

DETAILED DESCRIPTION OF THE INVENTION

In the following detailed description of the embodiments of the invention, numerous specific details are set forth in order to provide a thorough understanding of the embodiments of the invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

The embodiments of the invention include methods, apparatus, and systems for a compact capstan.

In one embodiment of the invention, a method of controlling a cable loop is provided using a slideable capstan. The method includes guiding a first portion of a cable loop to a slideable capstan using a first takeoff pulley and guiding a second portion of the cable loop to the slideable capstan using a second takeoff pulley; coupling the rotation of a shaft to the slideable capstan to rotate the slideable capstan; rotating the shaft in a first direction to draw in the first portion of the cable loop and feed out the second portion of the cable loop; and in response to the rotation of the capstan, moving the slideable capstan along the shaft to substantially maintain the positions of the first takeoff point and the second takeoff point relative to the first takeoff pulley and the second takeoff pulley, respectively.

In another embodiment of the invention, a capstan drive is provided that includes a cable receiving means to receive a cable loop; a moving means to move a take off point of the cable receiving means laterally as the cable receiving means is rotated; and a transmitting means to transmit a torsional force to rotate the cable receiving means. As the cable receiving means is rotated it is free to move laterally with respect to the transmitting means.

In another embodiment of the invention, a compact capstan drive is provided including a capstan support, a motor coupled to the capstan support, and a capstan coupled to the threaded portion of the capstan support. The capstan support has a threaded portion to receive a hub of the capstan. The motor has a drive shaft with an axis of rotation to rotate the capstan. The capstan includes a drum, a hub coupled to the drum, and a shaft coupled to the drive shaft of the motor. The drum of the capstan has a spiral groove on a cylindrical surface to receive a cable loop wound around the drum. The hub has a thread to engage the threaded portion of the capstan support. As the hub and the drum are rotated together, they move laterally along their length relative to the threaded support. The shaft of the capstan engages the drum and the hub to transmit a torsional force to rotate the drum and the hub. As they rotate, the drum and the hub are free to move along the length of the shaft.

In another embodiment of the invention, a compact capstan is provided including a drum, a threaded hub, and a shaft rotatably supported in a fixed relationship to a threaded support. The drum has a cylindrical surface, a first end, and an opposite second end. The cylindrical surface of the drum has a spiral or helical groove to receive a cable loop that is wound around the drum. The threaded hub is coupled to the first end of the drum and engages the threaded support. The threaded hub and the drum move together laterally along their length relative to the threaded support in response to their being rotated. The shaft engages the drum and the hub to transmit a torsional force to rotate the drum and the hub. The drum and the hub are free to move along the length of the shaft as they are rotated.

The detailed description describes the invention as it may be used in a laparoscopic surgery. It is to be understood that this is merely one example of the types of surgeries in which the invention may be used. The invention is not limited to laparoscopy nor to the particular structural configurations shown which are merely examples to aid in the understanding of the invention. Traditional minimally invasive surgery requires a high degree of surgical skill because the surgeon's hand movements are controlling a surgical tool at a substantial distance from the surgeon's hands, often requiring unnatural and non-intuitive hand motions. In robotically assisted surgery, a surgeon may operate a master controller to control the motion of surgical instruments at the surgical site. Servo mechanisms may move and articulate the surgical instrument based on the surgeon's manipulation of the hand input devices. The robotic assistance may allow the surgeon to control the motion of surgical instruments more easily and with greater precision.

Figure 1:
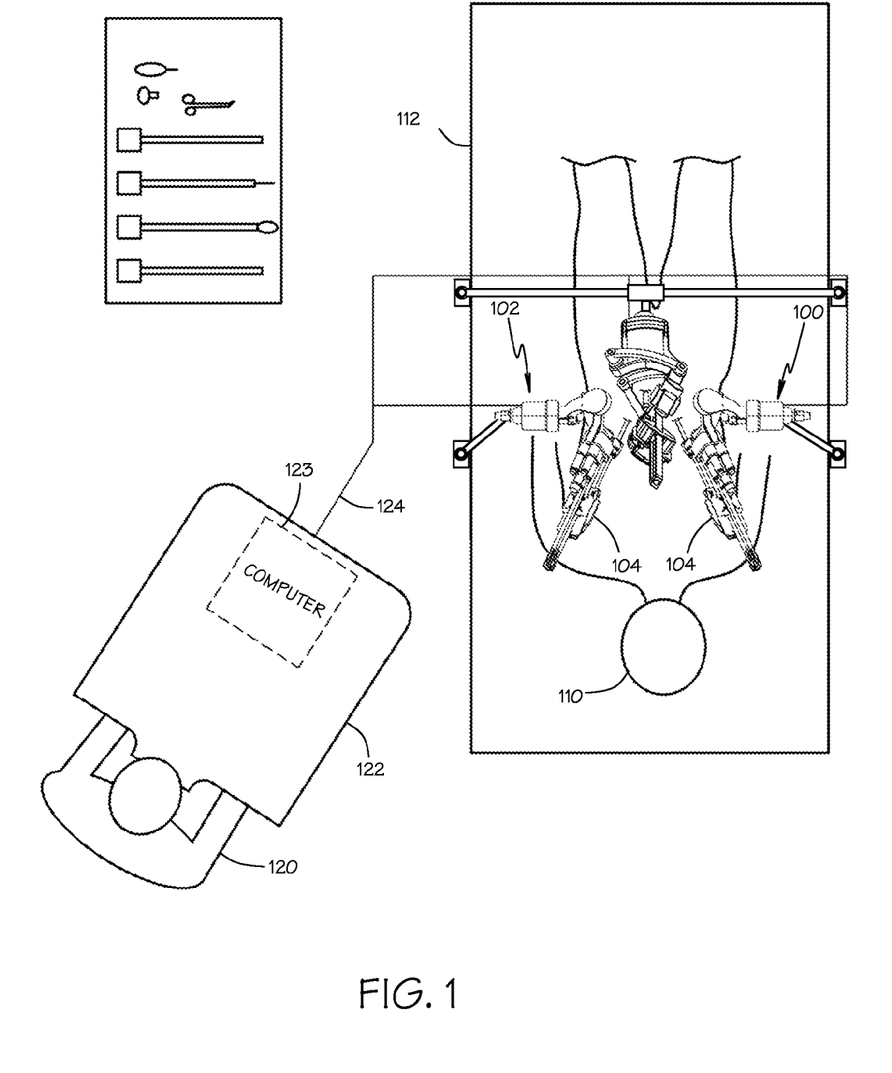
FIG. 1 is a plan view of a surgical suite in which embodiments of the invention are used.

FIG. 1 shows a schematic plan view of a surgical suite in which the invention may be used. A patient 110 is shown on an operating table 112 undergoing robotically assisted laparoscopic surgery. A surgeon 120 may use a master controller 122 to view a video image of the internal surgical site and control one or more surgical instruments and a laparoscopic camera by means of robotic servo mechanisms. The master controller 122 will typically include one or more hand input devices (such as joysticks, exoskeletal gloves, or the like) which are coupled by a servo mechanism to a surgical instrument. One or more robotic surgical arms 100, 102 may be used to support and move surgical instruments 104 at the surgical site during robotically assisted surgery.

Figures 2, 3, 4, 5:
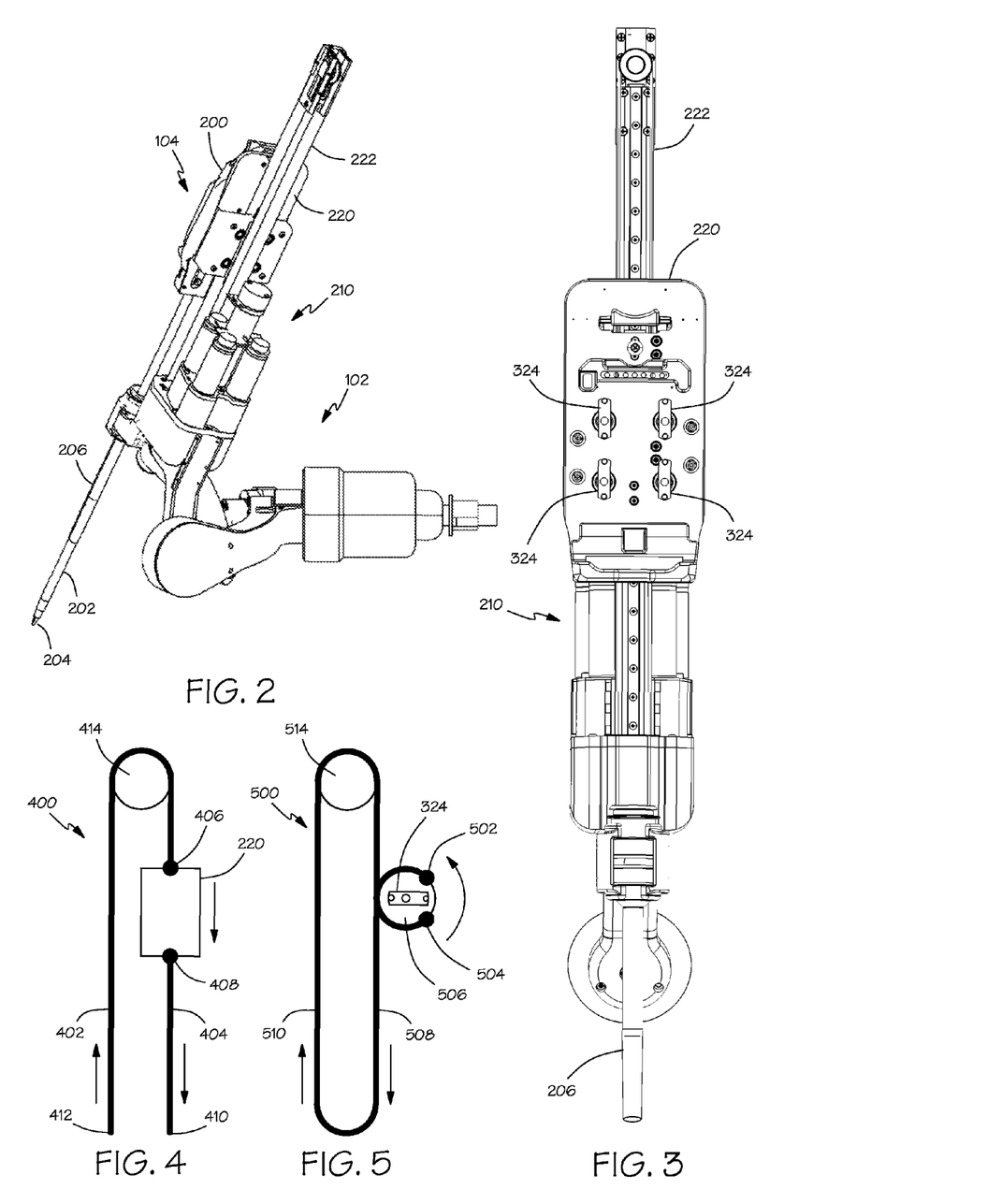
FIG. 2 is a pictorial view of a robotic surgical arm and surgical instrument from the operating suite of FIG. 1.
FIG. 3 is a plan view of a portion of the robotic surgical arm of FIG. 2 that supports the surgical instrument.
FIG. 4 is a schematic of a cable loop that provides lateral motion.
FIG. 5 is a schematic of a cable loop that provides rotary motion.

FIG. 2 shows a robotic surgical arm 102 supporting a surgical instrument 104. The surgical instrument 104 may include a head end 200 coupled to an end effector 204 by a tool shaft 202. The end effector 204 may be inserted into a surgical site through a cannula 206 that is supported by the robotic surgical arm 102. The end effector 204 at an internal end of the tool shaft 202 may provide any of a variety of surgical tools which may be actuated by servo mechanisms 210 which may be supported by the robotic surgical arm 102. The end effector 204 is coupled to a head end 200 of the surgical instrument 104 through the tool shaft 202. The head end 200 may include one or more drivers that control the movement of the end effector 204. Rotation of the drivers may be used to control the movement of the end effector 204.

The head end 200 of the surgical instrument 104 may be coupled to a tool carriage 220 on the robotic surgical arm 102. This may facilitate exchange of the surgical instrument 104 during the course of a surgical procedure. The tool carriage 220 may be slidingly supported by a spar 222 that is supported by the robotic surgical arm 102. The tool carriage 220 may be moved along the spar 222 to change the depth of insertion of the end effector 204 by moving the entire surgical instrument 104.

Referring to FIGS. 1 and 2, the robotic surgical arm 102 may include one or more servo motors 210 to move the surgical instrument 104 and/or the end effector 204 on the surgical instrument. One or more control wires 124 may provide signals between the computer 123 in the master controller 122 and the servo motors 210 on the robotic surgical arm 102. The master controller 122 may include a computer 123 to provide signals that control the servo mechanisms 210 of the surgical instrument 104 based on the surgeon's input and received feedback from the servo mechanisms.

FIG. 3 shows the spar 222, the tool carriage 220, and the servo motors 210 removed from the robotic surgical arm. The servo motors 210 may move the tool carriage 220 laterally along the spar 222. Movement of the tool carriage 220 along the spar 222 controls the depth of insertion of the surgical instrument that is connected to the tool carriage. The servo motors 210 may further move the end effector 204.

The end effector 204 may be moved by rotating receiving elements provided in the head end 200 of the surgical instrument 104. Each receiving element of the surgical instrument 104 may be coupled to a rotatable driver 324 provided on the tool carriage 220. The end effector 204 may be arranged such that approximately one revolution or less of the rotatable driver 324 moves the controlled motion of the end effector 204 through its full range. Thus, one or more servo motors 210 may be coupled to the surgical instrument 104 to control a motion of the end effector 204 or a rotation of the tool shaft 202.

FIG. 4 shows a schematic of a cable loop 400 that may be used to provide the lateral motion of the tool carriage 220 along the spar 222. For the purposes of this invention, a cable loop is used to describe a mechanical power transmission by means of a long flexible "cable", such as a wire or fiber cable or a thin flexible belt or band, that is driven such that one part of the cable is drawn in by the driving mechanism while an equal amount of the cable is fed out. This results in a motion of the cable comparable to the motion of a continuous loop of cable. However, for the purposes of this invention, the "cable loop" need not physically be in the form of a continuous loop of cable. The cable may also be tubing that transports fluids or gases to or from the surgical tool.

As shown in FIG. 4, the "cable loop" 400 may advantageously be provided by one or more cable segments 402, 404 that are coupled to provide the motion of a continuous loop of cable. In the schematic cable loop 400 of FIG. 4, the cable loop is provided by two cable segments 402, 404 each of which has an end 406, 408 that is coupled to the tool carriage 220. As a first end 410 of the cable is drawn in, a second end 412 of the cable is fed out and passed around an outboard pulley 414. This arrangement provides a controlled lateral movement of the tool carriage 220.

FIG. 5 shows a schematic of a cable loop 500 that may be used to provide the rotary motion of a rotatable driver 324. A single cable segment is shown with each of the two ends 502, 504 coupled to one of two coupled driver pulleys such that the pulleys are rotated as a first portion 508 of the cable 500 is drawn in while a second portion 510 of the cable is fed out and passed around an outboard pulley 514. It will be appreciated that two or more cable segments could be used to control the rotation of the rotatable driver 324 in an arrangement similar to that shown in FIG. 4. Likewise, a single cable segment in the arrangement shown in FIG. 5 could be used to control lateral movement of the tool carriage 220.

Figure 6:
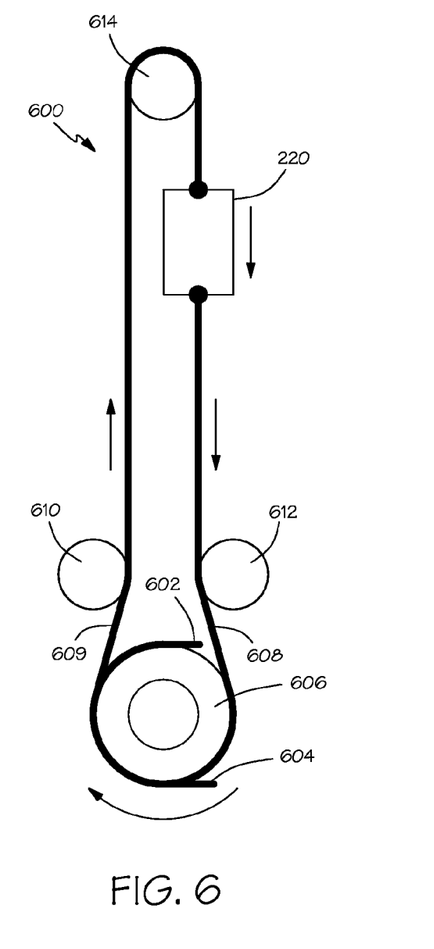
FIG. 6 is a schematic of another cable loop that provides lateral motion.

FIG. 6 shows a schematic of a cable loop 600 that may be used to provide a lateral movement of the tool carriage 220. The first 602 and second 604 ends of the cable loop 600 are wound around a capstan 606 and secured thereto. The capstan 606 provides a positive drive for drawing in a first portion 608 of the cable loop 600 while feeding out a second portion 609 of the cable at the same rate. The capstan 606 further provides spooling of the cable loop 600 as it is drawn in and unspooling of the cable as it is fed out. Two take off pulleys 610, 612 may be provided adjacent the capstan 606 to provide a stable path for the cable loop 600 as it passes to the outboard pulley 614 and to the tool carriage 220. Each end 602, 604 of the cable loop 600 may make one or more turns around the capstan 606 and then pass around one of the take off pulleys 610, 612 adjacent the capstan. Additional pulleys (not shown) may be provided between the take off pulleys 610, 612 and the tool carriage 220 to direct the cable loop 600 as required.

Figure 7:
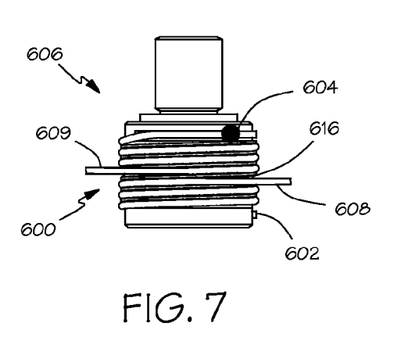
FIG. 7 is a side view of a capstan with a portion of a cable loop.

FIG. 7 shows a side elevation of the capstan 606 and a portion of the cable loop 600. The portions of the cable 608, 609 that extend to the take off pulleys 610, 612 have been shown as extending to the sides so that the point of take off 616 from the capstan 606 can be more easily seen. The point at which one end 604 of the cable may be secured to the capstan 606 is visible while the other end 602 of the cable may be secured to the capstan at the opposite end and on the opposite side such that it is not visible in this elevation. Alternatively, the cable may be attached at different places on the capstan or may not be attached to the capstan.

A coupled device, such as the tool carriage 220 or the rotatable driver 324, may be moved by rotating the capstan 606 to cause one portion 608 of the cable loop 600 to be drawn in and wound onto the capstan while unwinding and feeding out a second portion 609 of the cable loop. The capstan 606 may include a spiral or helical groove having a shape that receives the cable as it is wound onto the capstan. The spiral or helical groove may have a pitch, longitudinal spacing of adjacent sections of the groove, that allows the cable to be wound onto the capstan without overlaying adjacent turns of the cable. It will be appreciated that the take off point 616 for the cable loop 600 will move laterally along the capstan 606 as the cable is wound onto and around the capstan.

Figure 8:
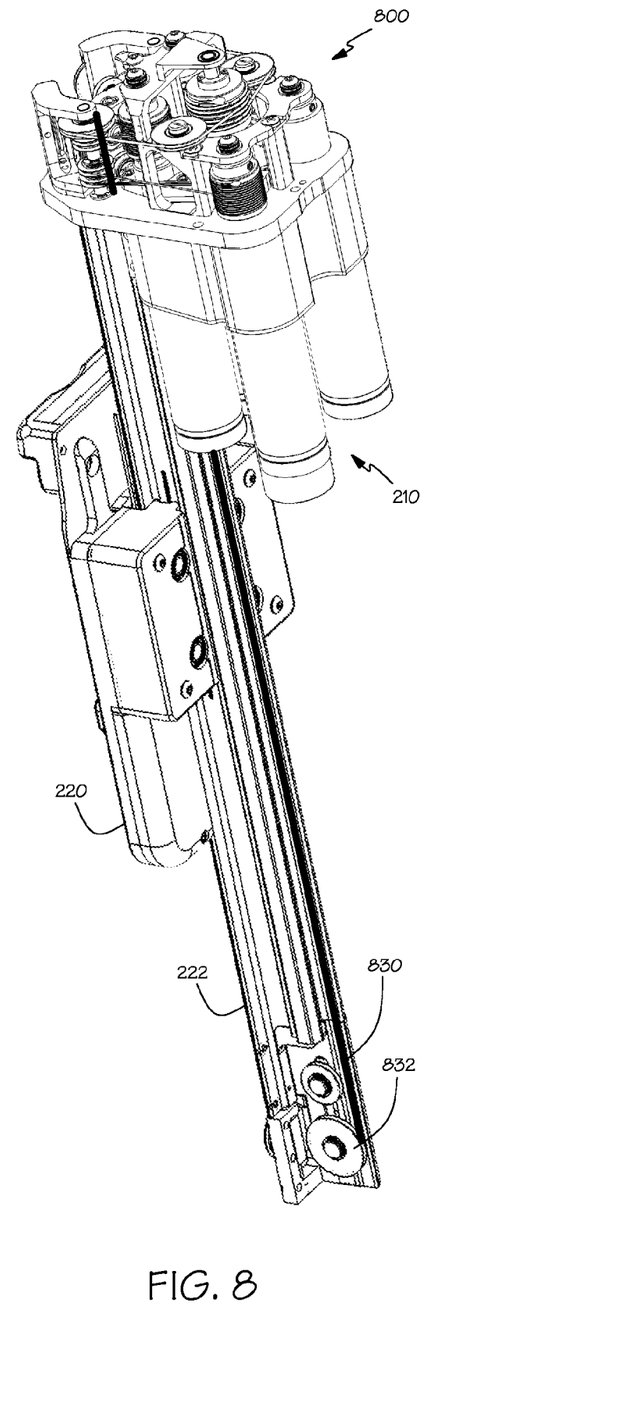
FIG. 8 is a pictorial view of a portion of the robotic surgical arm of FIG. 2 that supports the surgical instrument in which a cable drive system may be seen.
Figure 9:
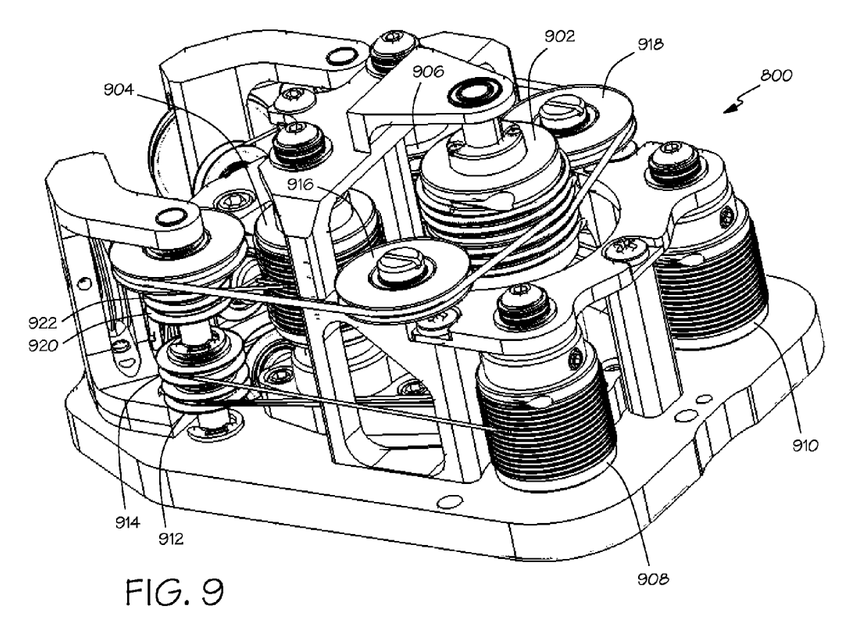
FIG. 9 is a pictorial view of a portion of FIG. 8 in which the cable drive system may be seen.

FIG. 8 shows a pictorial view of the spar 222, the tool carriage 220, and the servo motors 210 with the supporting structure removed so that capstans 800 which are driven by the servo motors may be seen. The capstans 800 are illustrated facing upward for clarity but they would typically face downward toward the patient in use. FIG. 9 shows a closer view of just the portion with the capstans 800. Five servo motors are shown driving five capstans. Two take off pulleys are provided for each capstan. Additional pulleys are provided to guide the cable through the spar.

Referring to FIG. 8, each of the servo motors 210 may provide a rotary motion that is coupled to the tool carriage 220 by a cable loop 830. For example, the cable loop 830 may pass over a pulley 832 at the end of the spar 222 remote from the servo motors 210. One of the instrument drivers 324 (see FIG. 3) on the tool carriage 220 may be coupled to the cable loop 830 such that movement of the cable loop by one of the servo motors 210 rotates the instrument driver. Additional cable loops (not shown) may be coupled to the remaining instrument drivers 324 on the tool carriage and to the tool carriage 220 itself such that movement of the additional cable loops by the associated servo motors 210 rotates the remaining drivers and moves the tool carriage along the spar 222.

Each servo motor 210 may drive one of the capstans 800, possibly through a gearbox (not shown). It may be appreciated from FIG. 8, which shows five servo motors 210 with their associated capstans and take off pulleys and additional pulleys for guiding the cables, that space is at a premium.

Referring to FIG. 9, it will be seen that the cables are directed from the capstans toward the spar (not shown) which is located toward the left in FIG. 9. Two of the capstans 904, 906 are adjacent the spar, two capstans 908, 910 are remote from the spar, and a fifth capstan 902 is between the other four capstans. For a capstan 908 that is remote from the spar, the take off pulleys 912, 914 may be a substantial distance from the capstan.

Figure 21:
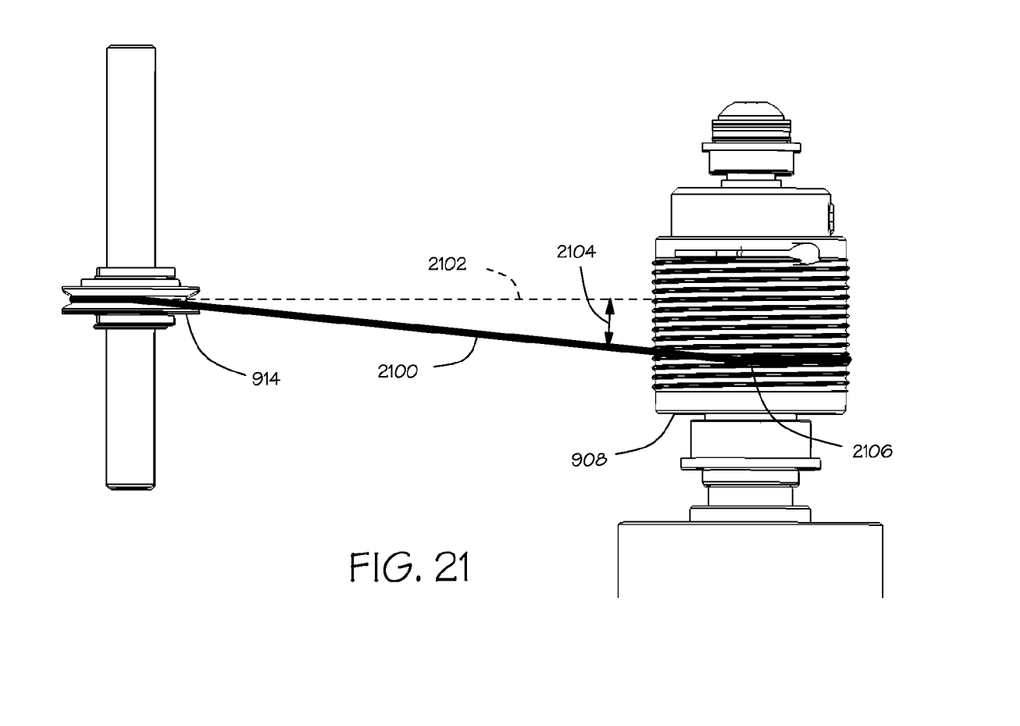
FIG. 21 is a side view of another capstan and take off pulley with a substantial distance between them.

As shown in FIG. 21, the lateral shift in the take off point 2106 of the cable loop 2100 from the capstan 908 as the cable loop is wound and unwound from the capstan creates only an acceptably small angle 2104 between the portion of the cable loop extending to the take off pulley 914 and the plane 2102 of the take off pulley, even when the cable is at the extremes of its travel on the capstan. A small angle 2104 between the cable 2100 and the plane 2102 of the take off pulley 914 is acceptable. An angle of approximately five degrees may be acceptable for a typical configuration.

Figures 10, 11:
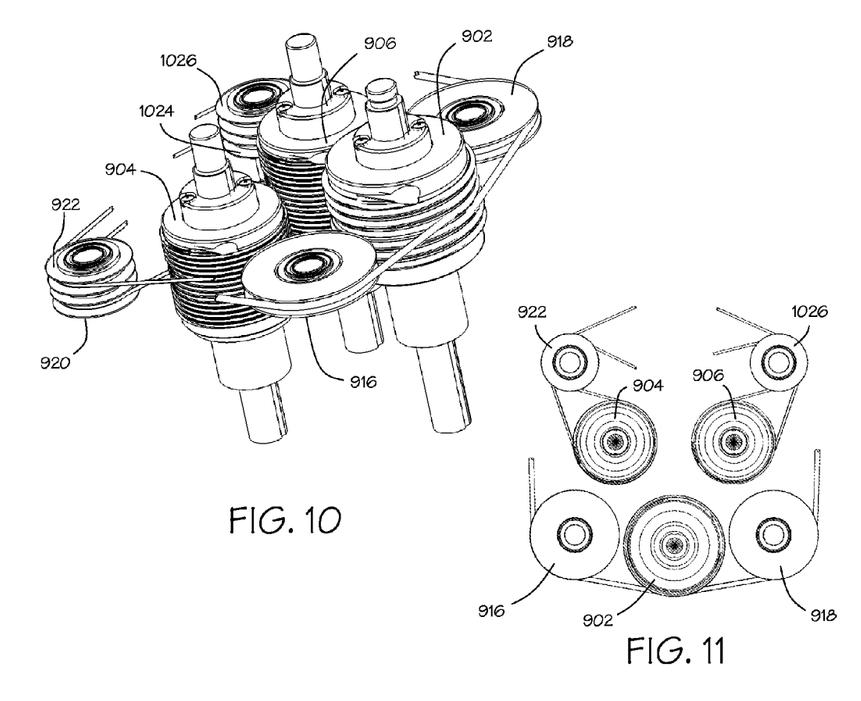
FIG. 10 is a pictorial view of a portion of the cable drive system of FIG. 9.
FIG. 11 is a plan view of the portion of the cable drive system of FIG. 10.

In contrast, the remaining three capstans 902, 904, 906 are close to their take off pulleys 916, 918, 920, 922, 1024, 1026 that receive the cable loops from these capstans.

FIG. 10 shows these three capstans and their take off pulleys. FIG. 11 is a plan view of these three capstans and their take off pulleys which shows the short distance between the capstan and the take off pulleys. The distance between each capstan and its associated take off pulleys may be comparable to the distance between the take off points when the cable is at the extremes of its travel on the capstan.

Figure 12:
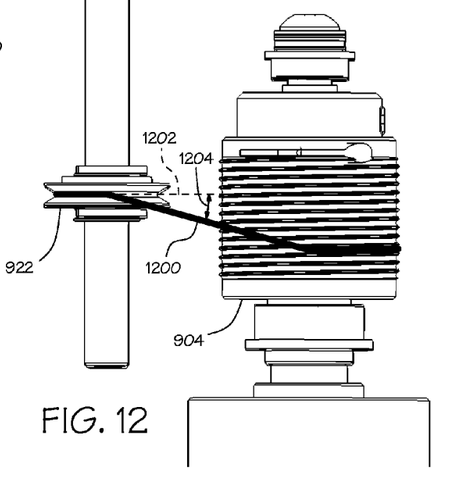
FIG. 12 is a side view of a capstan and take-off pulley.

FIG. 12 is a side elevation of a capstan 904 that is close to its take off pulley 922. This creates a relatively large angle 1204 between the cable 1200 and the plane 1202 of the take off pulley 922 when the cable is at the extremes of its travel on the capstan 904. It will be appreciated that a large angle 1204 between the cable 1200 and the plane 1202 of the take off pulley 922 causes unbalanced forces on the take off pulley that can increase friction and cause wear in the system. The size of angle 1204 between the cable 1200 and the plane 1202 of the take off pulley 922 that becomes unacceptable depends on a variety of factors, such as the load on the cable and configuration of the pulleys. The cable 1200 may run off the capstan groove or the take off pulley 922 if the angle between the cable and the plane of the take off pulley 1202 is too great. An angle 1204 between the cable 1200 and the plane 1202 of the take off pulley 922 increases the length of the cable loop, which may require some form of tension compensating device. The capstan 904 and take off pulley 922 configuration shown may be unworkable if the cable 1200 is allowed to form the angle 1204 shown to the plane 1202 of the take off pulley 922.

Figure 13:
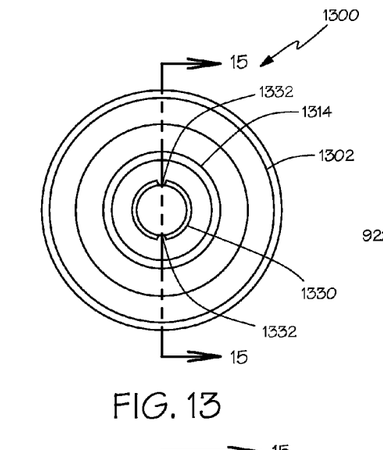
FIG. 13 is an end view of a compact capstan assembly.
Figure 14:
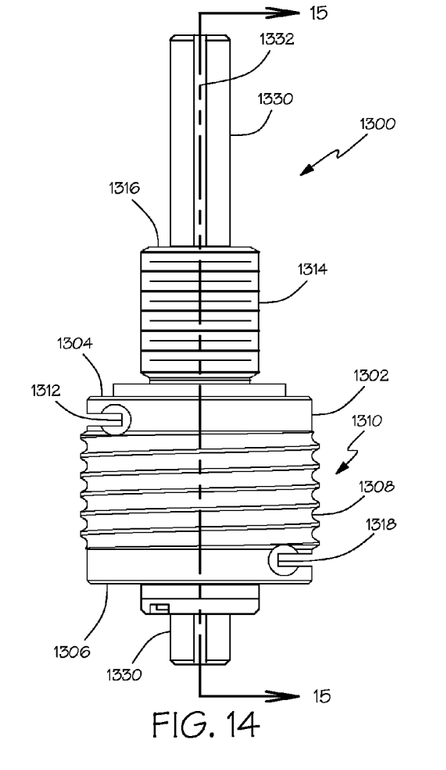
FIG. 14 is a side view of the compact capstan assembly of FIG. 13.
Figure 15:
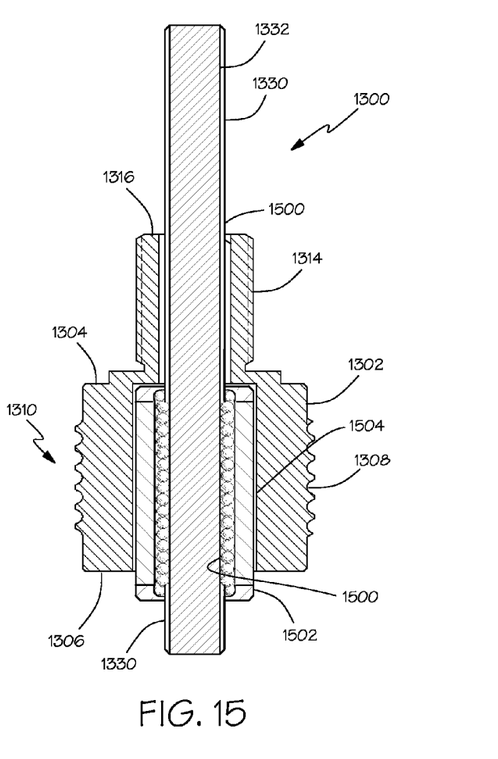
FIG. 15 is a side section view of the compact capstan assembly of FIG. 13 along section line 15-15.

FIGS. 13 through 15 show a compact capstan 1300 with FIG. 13 being an end view, FIG. 14 being a side view, and FIG. 15 being a sectioned view from the side. The compact capstan 1300 includes a drum 1310 that is generally in the form of a cylinder having a cylindrical surface 1302, a first end 1304, and an opposite second end 1306. A spiral or helical groove 1308 is provided in the cylindrical surface 1302 of the drum into which a cable loop may be wound. The cable loop may be discontinuous with two ends of segments of the cable loop being secured to opposite ends 1312, 1318 of the spiral or helical groove 1308. This configuration of the cable loop may permit the two segments of the cable loop to take off from the capstan at approximately the same lateral position along the length of the drum as may be seen in FIG. 10.

A threaded hub 1314 is coupled to the first end 1304 of the drum 1310. The threaded hub 1314 may include a synchronization thread with substantially the same pitch as the spiral or helical groove 1308. In the configuration shown, the thread is an external thread but an internal thread may be used in other configurations. The thread may be a sixty degree Unified National thread, a metric thread, an Acme thread, or other form of screw thread.

Figure 18A:
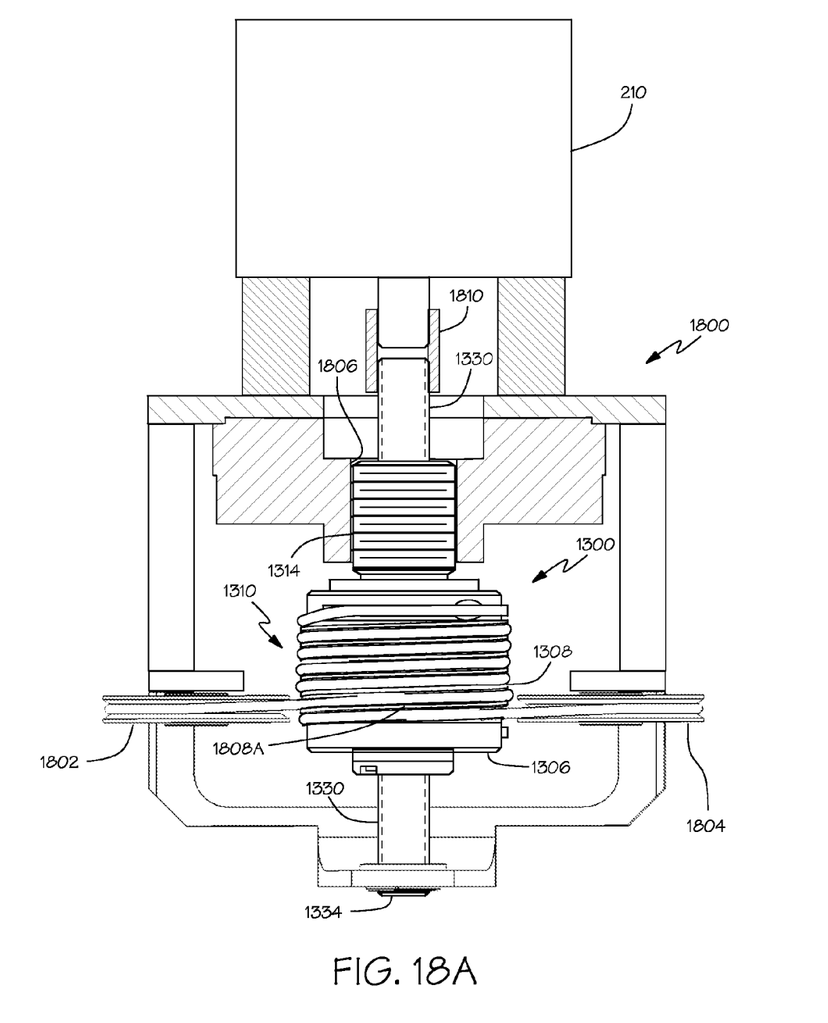
FIG. 18A is a side view of the compact capstan assembly of FIG. 14 at a first position in a threaded support structure with a portion shown as a section view.
Figure 18B:
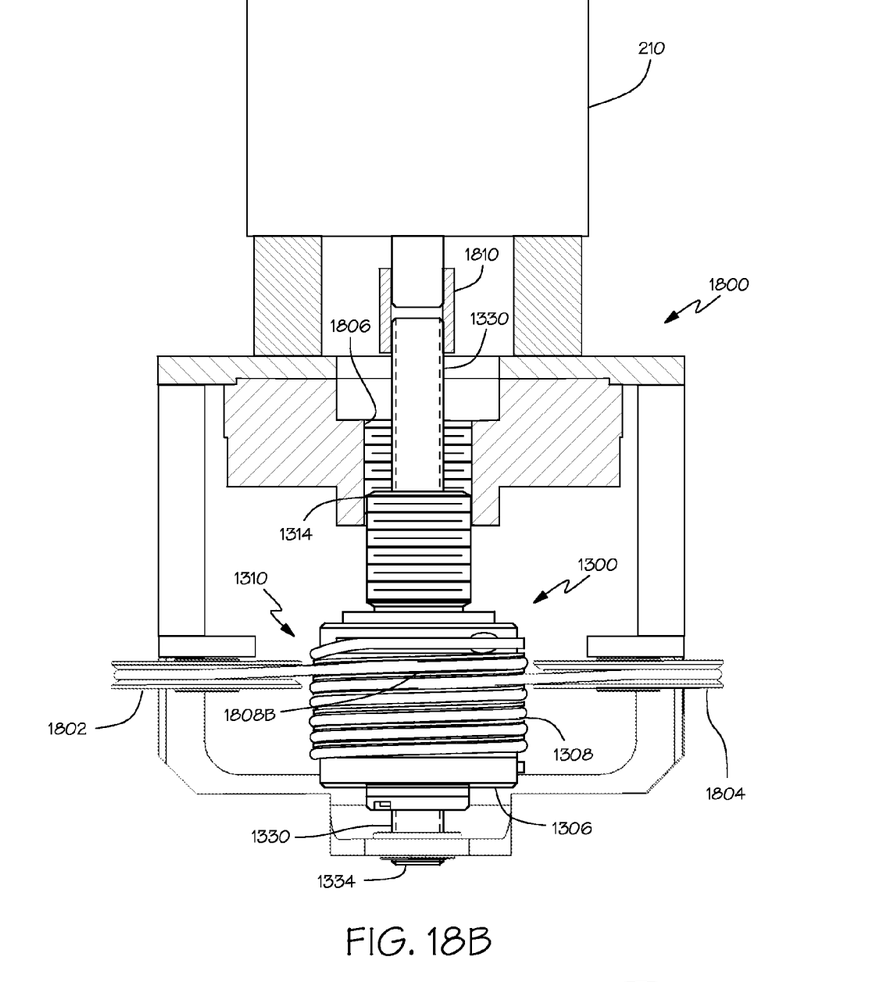
FIG. 18B is a side view of the compact capstan assembly of FIG. 14 at a second position in the threaded support structure with a portion shown as a section view.

As shown in FIGS. 18A and 18B, the threaded hub 1314 engages a threaded support 1800. As the threaded hub 1314 and the drum 1310 are rotated, they move laterally along their length relative to the threaded support 1800. As discussed further below, this may maintain a substantially constant angle between the cable and the plane of the take off pulley.

A splined passage 1500 extends through the drum 1310 and threaded hub 1314 from an end 1306 of the drum to an opposing end 1316 of the hub. A splined shaft 1330 has a length that is greater than a length of the splined passage 1500. The splined shaft 1330 passes through the splined passage 1500 extend. The splined shaft 1330 extends beyond both ends 1206, 1316 of the splined passage 1500. The splined shaft 1330 transmits a torsional force to the drum 1310 and the threaded hub 1314 which remain free to move laterally along the splined shaft.

The splined shaft 1330 may provide one or more grooves 1832 or projections that extend along the length of the splined shaft. The splined passage 1500 may provide one or more projections or grooves that mate with the respective grooves or projections of the splined shaft 1330 to provide positive transmission of torsional forces to the drum 1310 and the threaded hub 1314.

A particularly advantageous form of splined shaft and passage for use in the present invention is a ball spline assembly. As may be seen in FIG. 15, a ball spline assembly may include a splined shaft 1330 and a ball spline nut 1502. The ball spline nut may include a number of recirculating balls 1500 as the projections that mate with a groove 1832 in the splined shaft 1330. Ball spline assemblies provide nearly friction-free linear motion while simultaneously transmitting torsional loads. The spline nut 1502 may be preloaded to decrease the radial play in the ball spline assembly and provide low backlash.

FIG. 15 is a section view of the side elevation of the compact capstan assembly 1300. A portion 1504 of the splined passage 1500 that is within the drum 1310 may be enlarged to receive the spline nut 1502, which may have a diameter that is similar to the diameter of the hub portion 1314. The spline nut 1502 may be fixed within the splined passage 1500 by any of a variety of means, such as a set screw. The spline nut 1502 may move in unison with the drum 1310. The portion of the splined passage 1500 within the threaded hub 1314 may have a diameter that is only sufficient to receive the splined shaft 1330.

Figure 16:
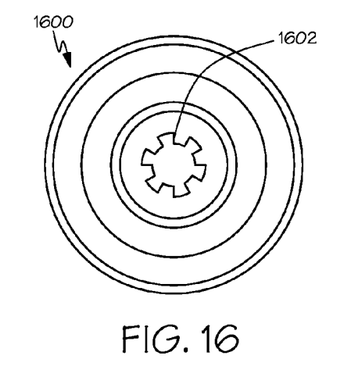
FIG. 16 is an end view of another compact capstan assembly.
Figure 17:
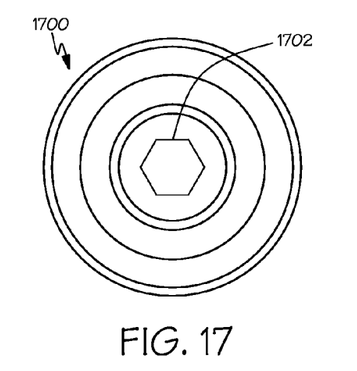
FIG. 17 is an end view of another compact capstan assembly.

FIG. 16 shows an end view of a hub 1600 that includes a conventional splined passage 1602. FIG. 17 shows an end view of a hub 1700 that includes a hexagonal shaped passage 1702. It will be appreciated that the shaft and passage can take any of a variety of forms. The passage will engage the shaft such that the shaft can transmit a torsional force to the drum and the hub which are free to move along the length of the shaft.

FIGS. 18A and 18B show a compact capstan assembly 1300 in a threaded support structure 1800. The threaded support structure 1800 provides a threaded passageway 1806 to receive the threaded hub 1314 of the capstan assembly 1300. The threaded support structure 1800 may also support a motor assembly 210, two take off pulleys 1802, 1804, and the end 1334 of the splined shaft 1330 that emerges from the drum end 1306 of the capstan assembly 1300. The portion of the threaded support structure 1800 providing the threaded passageway 1806 and the support and coupling 1810 of the motor assembly 210 are shown in cross-section along the diameter of the threaded passageway and the remainder of the elements are shown in full elevations.

The motor assembly 210 may include a gear box such that the shaft that emerges from the assembly provides a higher torque and a slower rotational speed than the shaft of the motor itself. The splined shaft 1330 is fixedly coupled to a shaft of the motor assembly 210 such that the splined shaft is an extension of the motor assembly shaft. It may be appreciated that the threaded support structure 1800 may hold all the components in a fixed relationship to one another except for the compact capstan assembly 1300.

As may be seen in FIGS. 18A and 18B the threaded hub 1314 and drum 1310 move laterally along the length of the splined shaft 1330 as the capstan assembly 1300 is rotated. This is because the threads of the hub 1314 couple to the threaded passageway 1806 of the threaded support structure 1800. FIGS. 18A and 18B may represent the two extremes of travel of the threaded hub 1314 and drum 1310 with respect to the support structure.

It will be seen that the take off point 1808A, 1808B for the cable moves along the length of the drum 1310 as the drum rotates between the two extremes of travel. It will further be seen that the drum 1310 moves laterally at a similar rate as the take off point 1808A, 1808B for the cable moves because the threaded hub 1314 has substantially the same pitch as the spiral or helical grove 1308 on the drum 1310 in which the cable is wound. As a result, the take off point 1808A, 1808B for the cable remains at substantially the same lateral position relative to the threaded support structure 1800 and more particularly relative to the take off pulleys 1802, 1804. This permits the take off pulleys 1802, 1804 to be placed a short distance away from the capstan 1300 because rotation of the capstan will not result in a large angle between the cable and the plane of the take off pulleys. Moreover the angle between the cable and the plane of the take off pulleys may be essentially constant over the entire range of motion of the compact capstan 1300.

The take off pulleys 1802, 1804 and the splined shaft 1330 are coupled to the threaded support structure 1800 so they are free to rotate while being constrained against lateral movement. It will be appreciated that only the threaded hub 1314, drum 1310, and spline nut 1502 can move laterally relative to the threaded support structure 1800. This may simplify the connection between the motor assembly 210 and the capstan assembly 1300 because the motor assembly may be coupled to the splined shaft 1330 and supported by the threaded support structure 1800. This is possible because there is no lateral motion of the splined shaft 1330 relative to the motor assembly 210 or the threaded support structure 1800.

Figure 19:
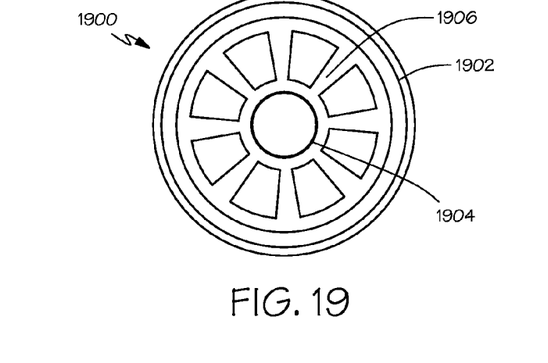
FIG. 19 is an end view of another compact capstan assembly.

FIG. 19 shows an end view of a capstan and shaft assembly 1900 that provides another form of coupling between the capstan 1902 and the shaft 1904. A disk-like flexure 1906 is attached to the capstan at the outside diameter of the flexure. The shaft 1904 passes through a central hole in the flexure 1906 and is attached to the flexure along the edge of the central hole. The flexure 1906 has a series of spokes that join the inner and outer portions of the flexure. The spokes make the flexure 1906 compliant along the axis of the shaft 1904 while maintaining a high torsional stiffness. Thus the shaft 1904 can transmit a torsional force to the drum and the hub of the capstan 1902 which is free to move along the length of the shaft within the limits of the flexure's 1906 axial compliance.

The flexure 1906 may provide a limited range of axial motion as compared to configurations that use a splined shaft. Configurations employing a flexure 1906 to couple the capstan 1902 to the shaft 1904 may only provide a moderate shifting of the capstan. In some configurations the hub may have a smaller pitch than the groove in the hub. Thus the capstan will slide to reduce some but not all of the angle between the cable and the plane of the take off pulley. This may maintain the angle within an acceptable range. An angle of approximately five degrees may be acceptable for a typical configuration.

Two flexures 1906, spaced some distance apart, may couple the capstan 1902 to the shaft 1904. This may provide radial support for the capstan 1902.

In another configuration, a single flexure 1906 may couple the capstan 1902 to the shaft 1904 at one end of the capstan 1902. The capstan 1902 may include a passage with a slip fit on the shaft that enables axial sliding and provides radial support.

Figure 20:
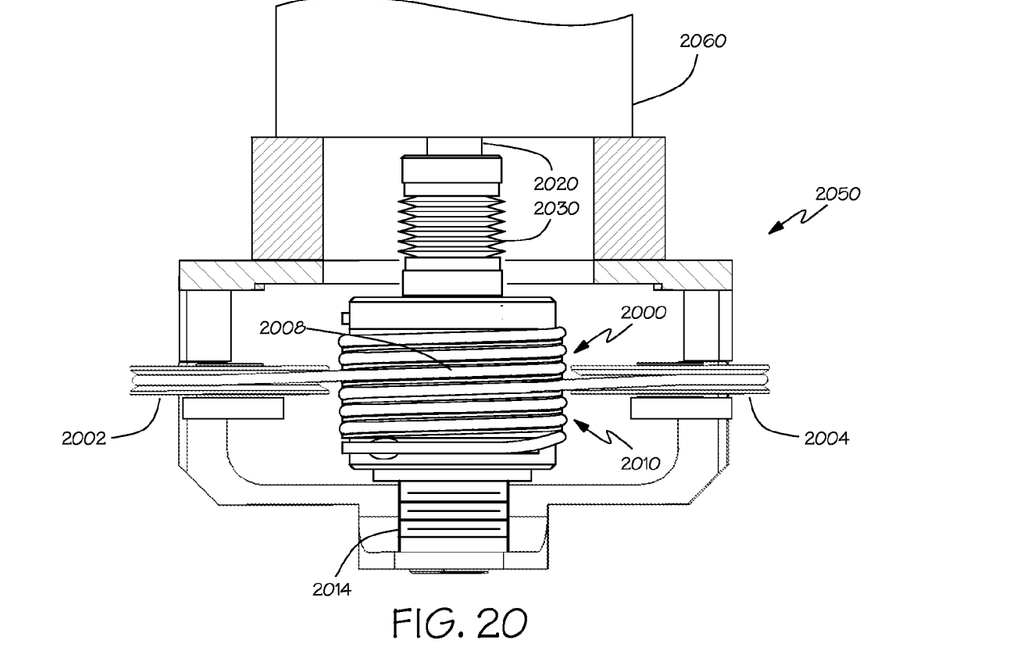
FIG. 20 is a side view of another capstan and take off pulley with a portion shown as a section view.

FIG. 20 shows another compact capstan assembly 2000 in a threaded support structure 2050. The threaded support structure 2050 provides a threaded post 2014 that engages a threaded passageway of the capstan assembly 2000. The threaded support structure 2050 may also support a motor assembly 2060, and two take off pulleys 2002, 2004.

In comparison to the threaded support structure 1800 shown in FIGS. 18A and 18B, the threaded post 2014 in the configuration shown in FIG. 20 is on the opposite side of the support structure 2050 from the motor assembly 2060.

In the configuration shown, the shaft 2020 of the motor assembly 2060 is coupled to the capstan 2000 by a bellows 2030. The bellows can transmit a torsional force to the drum and the hub of the capstan 2000 which is free to move along an axis defined by the motor shaft 2020 within the limits of the bellows' extension.

It may be appreciated that the threaded support structure 2050 may hold all the components in a fixed relationship to one another except for the compact capstan assembly 2000. The capstan 2010 moves laterally along the length of threaded post 2014 as the capstan assembly 2000 is rotated. As in the previous configuration, the take off point 2008 for the cable remains at substantially the same lateral position relative to the threaded support structure 2050 and, more particularly, relative to the take off pulleys 2002, 2004. Only the capstan assembly 2000 moves laterally relative to the threaded support structure 2050.

In another configuration (not shown), the threaded support structure provides a threaded passageway rather than a threaded post on the opposite side of the support structure from the motor assembly. The compact capstan assembly in this configuration may be similar to the compact capstan assembly 1800 shown in FIGS. 18A and 18B. However, the threaded passageway supports the threaded hub that, in turn, supports the outboard end of the splined shaft. This may eliminate the need for an outboard bearing to support the outboard end of the splined shaft.

While certain exemplary embodiments have been described and shown in the accompanying drawings, it is to be understood that such embodiments are merely illustrative of and not restrictive on the broad invention. For example, while an externally threaded hub is shown coupled to an internally threaded passage in the support structure, the capstan may provide an internally threaded hub that is coupled to a threaded post on the support structure. This invention is not limited to the specific constructions and arrangements shown and described, since various other modifications may occur to those ordinarily skilled in the art.

What is claimed is:

1. A compact capstan comprising:
   a cable loop having a first end and a second end;
   a drum having a cylindrical surface, a first end, and an opposite second end, the cylindrical surface of the drum having a spiral groove to receive the first end of the cable loop attached to a first cable attachment point at a first end of the spiral groove and the second end of the cable loop attached to a second cable attachment point at a second end of the spiral groove with a loop portion of the cable loop that is fed out at one end and drawn in at an opposite end between the first and second ends of the spiral groove such that the loop portion maintains a constant length;
   a threaded hub coupled to the first end of the drum, the threaded hub to engage a threaded support, the threaded hub and the drum to move together laterally along their length relative to the threaded support in response to being rotated; and
   a splined shaft rotatably supported in a fixed relationship to the threaded support, the splined shaft engaging a ball spline nut coupled to the drum and the hub to transmit a torsional force to rotate the drum and the hub, the ball spline nut, the drum and the hub being free to move along the length of the splined shaft.

2. The compact capstan of claim 1, wherein the ball spline nut has a diameter that is similar to a diameter of the hub and the ball spline nut is located substantially within the drum.

3. The compact capstan of claim 1, wherein the drum and hub include a passage extending from an end of the drum through to an end of the hub furthest from the drum, and the shaft has a length that is substantially greater than a length of the passage, the shaft passing through the passage and extending beyond both ends of the passage.

4. The compact capstan of claim 1, the hub includes a thread with substantially the same pitch as the spiral groove of the drum.

5. A compact capstan drive comprising:
a capstan support having a threaded portion;
a motor coupled to the capstan support, the motor having a drive shaft with an axis of rotation;
a cable loop having a first end and a second end;
a capstan coupled to the threaded portion of the capstan support, the capstan including
a drum having a spiral groove on a cylindrical surface, the spiral groove to receive the first end of the cable loop attached to a first cable attachment point at a first end of the spiral groove and the second end of the cable loop attached to a second cable attachment point at a second end of the spiral groove with a loop portion of the cable loop that is fed out at one end and drawn in at an opposite end between the first and second ends of the spiral groove such that the loop portion maintains a constant length;
a hub coupled to the drum, the hub having a thread to engage the threaded portion of the capstan support, the hub and the drum to move laterally along their length relative to the threaded support in response to being rotated; and
a splined shaft coupled to the drive shaft of the motor, the splined shaft engaging a ball spline nut coupled to the drum and the hub to transmit a torsional force to rotate the drum and the hub, the ball spline nut, the drum and the hub being free to move along the length of the splined shaft.

6. The compact capstan drive of claim 5, wherein the ball spline nut has a diameter that is similar to a diameter of the hub and the ball spline nut is located substantially within the drum.

7. The compact capstan drive of claim 5, further comprising two take off pulleys rotatably coupled to the support structure, one end of the loop portion of the cable loop extending from a first of the two take off pulleys and the opposite end of the loop portion of the cable loop extending from a second of the two take off pulleys.

8. The compact capstan drive of claim 5, wherein the spiral groove of the drum has substantially the same pitch as the threaded passage.

9. The compact capstan drive of claim 5, wherein the drum and the hub include a passage extending from an end of the drum through to an end of the hub furthest from the drum, and the shaft has a length that is substantially greater than a length of the passage, the shaft passing through the passage and extending beyond both ends of the passage.

10. A compact capstan drive comprising:
a cable loop having a first end and a second end;
a cable receiving means to receive the cable loop, the cable receiving means including a first end receiving means to receive the first end of the cable loop and a second end receiving means to receive the second end of the cable loop with a loop portion of the cable loop that is fed out at one end and drawn in at an opposite end by the cable receiving means between the first and second ends such that the loop portion maintains a constant length;
a moving means to move a take off point of the cable receiving means laterally as the cable receiving means is rotated; and
a transmitting means to transmit a torsional force to rotate the cable receiving means, as it is rotated the cable receiving means is free to move laterally with respect to the transmitting means, the transmitting means including a splined shaft and a ball spline nut that engages the splined shaft.

11. The compact capstan drive of claim 10, claim 16, wherein the ball spline nut is located substantially within the cable receiving means.

12. The compact capstan drive of claim 10, wherein the cable receiving means further includes an end receiving means to receive an end of a segment of the cable loop.

13. The compact capstan drive of claim 10, further including a providing means to provide the torsional force to the cable receiving means.

14. The compact capstan drive of claim 10, further including a supporting means to support the providing means and the cable receiving means, wherein the providing means being fixed to the supporting means and the cable receiving means being fixed axially but not laterally to the supporting means.

15. The compact capstan drive of claim 14, further including a guiding means to guide the cable loop to and from the cable receiving means.

16. The compact capstan drive of claim 15, wherein the guiding means is fixed laterally to the supporting means.

17. A method of controlling a cable loop having a first end and a second end, the method comprising:
receiving the cable loop in a spiral groove on a cylindrical surface of a drum;
attaching the first end of the cable loop to a first cable attachment point at a first end of the spiral groove;
attaching the second end of the cable loop to a second cable attachment point at a second end of the spiral groove;
providing a loop portion of the cable loop that is fed out at one end and drawn in at an opposite end between the first and second ends of the spiral groove such that the loop portion maintains a constant length;
rotating a splined shaft that engages a ball spline nut coupled to the drum to transmit a torsional force while leaving the drum free to move laterally on the splined shaft; and
moving the drum laterally on the splined shaft by a threaded hub coupled to the first end of the drum, the threaded hub engaging a threaded support such that the ball spline nut, the threaded hub and the drum move together laterally along their length relative to the threaded support in response to the ball spline nut, the threaded hub and the drum being rotated by the splined shaft.

18. The method of claim 17, further including guiding the cable loop to and from the drum with two takeoff pulleys, one end of the loop portion of the cable loop extending from a first of the two take off pulleys and the opposite end of the loop portion of the cable loop extending from a second of the two take off pulleys.

19. The method of claim 17, further including energizing a motor coupled to the splined shaft to rotate the splined shaft.

* * * * *